United States Patent
Gunji et al.

(10) Patent No.: US 8,366,621 B2
(45) Date of Patent: Feb. 5, 2013

(54) ULTRASONIC DIAGNOSTIC APPARATUS AND MEDICAL IMAGE DISPLAY APPARATUS

(75) Inventors: Takayuki Gunji, Otawara (JP); Jiro Higuchi, Otawara (JP); Eiji Goto, Otawara (JP); Osamu Nakajima, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1110 days.

(21) Appl. No.: 12/238,940

(22) Filed: Sep. 26, 2008

(65) Prior Publication Data

US 2009/0082675 A1    Mar. 26, 2009

(30) Foreign Application Priority Data

Sep. 26, 2007 (JP) ................. 2007-249874

(51) Int. Cl.
*A61B 8/00* (2006.01)

(52) U.S. Cl. ........ 600/439; 600/437; 600/443; 600/449; 600/450

(58) Field of Classification Search .................. 600/407, 600/437, 439, 443, 449, 450
See application file for complete search history.

(56) References Cited

U.S. PATENT DOCUMENTS

| | | | |
|---|---|---|---|
| 6,761,689 B2 * | 7/2004 | Salgo et al. | 600/447 |
| 2002/0072672 A1 * | 6/2002 | Roundhill et al. | 600/450 |

FOREIGN PATENT DOCUMENTS

| | | |
|---|---|---|
| CN | 1820711 A | 8/2006 |
| JP | 4-174658 | 6/1992 |
| JP | 7-59777 | 3/1995 |
| JP | 9-192130 | 7/1997 |
| JP | 2001-14495 | 1/2001 |
| JP | 2001-175847 | 6/2001 |
| JP | 2006-6932 | 1/2006 |
| JP | 2006-523510 | 10/2006 |
| WO | WO 2006/027899 A1 | 3/2006 |

OTHER PUBLICATIONS

Japanese Office Action issued May 15, 2012, in Japan Patent Application No. 2007-249874 (with English translation).

* cited by examiner

*Primary Examiner* — Brian Casler
*Assistant Examiner* — Joel Lamprecht
(74) *Attorney, Agent, or Firm* — Oblon, Spivak, McClelland, Maier & Neustadt, L.L.P.

(57) ABSTRACT

A transmission and reception unit repeatedly scans a three-dimensional scanning area including a specific part of a patient with an ultrasonic beam via an ultrasonic probe. A volume data set generation unit generates a plurality of volume data sets whose scanning times different from one another in accordance with the output from the transmission and reception unit. A section image generation unit respectively generates the data of a plurality of the section images concerning the predetermined section of the specific part based on the plurality of the volume data sets. An image display unit displays the plurality of section images by changing at least one of the position and the size of each of the plurality of section images against the display area in accordance with variation of at least one of the position and the shape of the specific part on the plurality of section images.

15 Claims, 6 Drawing Sheets

ULTRASONIC DIAGNOSTIC APPARATUS AND MEDICAL IMAGE DISPLAY APPARATUS

CROSS-REFERENCE TO RELATED APPLICATIONS

This application is based upon and claims the benefit of priority from prior Japanese Patent Application No. 2007-249874, filed Sep. 26, 2007, the entire contents of which are incorporated herein by reference.

BACKGROUND OF THE INVENTION

1. Field of the Invention

The present invention relates to an ultrasonic diagnostic apparatus and a medical image display apparatus which process a volume data set generated by ultrasonic scanning of an area in which an organ moves with time elapse in a patient, and especially the area including a heart.

2. Description of the Related Art

There is a case that an ultrasonic diagnostic apparatus generates a plurality of volume data sets (time series volume data) whose scanning times of the heart are different from one another by performing a three-dimensional scanning of a patient and displays a desired section image concerning the plurality of volume data sets. At this time, it is common to display an A section image and a B section image concerning a long axis section of the heart and a C section image concerning a short axis section with a MPR (Multi Planar Reformat).

On the other hand, there are various methods for displaying various organ images in a volume data set which is generated by a medical image generation apparatus such as an ultrasonic diagnostic apparatus while changing a viewpoint (see Jpn. Pat. Appln. KOKAI Publication Nos. 2001-14495 and 2001-175847).

As is generally known, the heart vigorously moves in a body of a patient due to beating. Therefore, following problems occur at the time of displaying an image of the heart.

(1) The heart protrudes from a display area on the C section image, especially on the C section image at a diastole.

(2) In relation to item (1), the heart is displayed small on the C section image at a systole when the scanning position is adjusted so that the heart does not protrude from the display area.

(3) The entire C section image is displayed small because the C section image is displayed in accordance with a depth value.

(4) The scanning range becomes broad because the entire spatial moving range of the heart is scanned. Accordingly, the frame rate is decreased.

BRIEF SUMMARY OF THE INVENTION

It is an object of the present invention to provide an ultrasonic diagnostic apparatus and a medical image display apparatus which are capable of displaying various section images concerning a specific part whose position and shape vary with time elapse in accordance with the variation of the position and the shape.

An ultrasonic diagnostic apparatus according to a first aspect of the present invention comprises: an ultrasonic probe which transmits and receives ultrasonic waves; a transmission and reception unit which repeatedly scans a three-dimensional scanning area including a specific part of a patient with an ultrasonic beam via the ultrasonic probe; a volume data set generation unit which generates a plurality of volume data sets whose scanning times different from one another based on output from the transmission and reception unit; a section image generation unit which respectively generates data of a plurality of section images concerning one section of the specific part based on said plurality of the volume data sets; and a display unit which displays said plurality of section images by changing at least one of the position and the size of each of said plurality of section images against a display area in accordance with the variation of at least one of the position and the shape of the specific part on said plurality of section images.

An ultrasonic diagnostic apparatus according to a second aspect of the present invention comprises: an ultrasonic probe which transmits and receives an ultrasonic beam against a three-dimensional scanning area including the heart of a patient; a volume data set generation unit which generates a plurality of volume data sets whose scanning times different from one another based on output of the ultrasonic probe; a short axis image generation unit which respectively generates data of a plurality of short axis images concerning a predetermined short axis section of the heart based on said plurality of volume data sets; and a scanning control unit which changes scanning line density in the scanning range based on a range of the specific part appearing on each of said plurality of short axis images and the scanning range.

An ultrasonic diagnostic apparatus according to a third aspect of the present invention comprises: an ultrasonic probe which transmits and receives an ultrasonic beam against a three-dimensional scanning range including the heart of a patient; a volume data set generation unit which generates a plurality of volume data sets whose scanning times different from one another based on output of the ultrasonic probe; a short axis image generation unit which respectively generates data of a plurality of short axis images concerning a predetermined short axis section of the heart based on said plurality of volume data sets; and a scanning control unit which changes the scanning range in accordance with the position variation of the heart on said plurality of short axis images with time elapse.

An ultrasonic diagnostic apparatus according to a fourth aspect of the present invention comprises: an ultrasonic probe which transmits and receives an ultrasonic beam against a three-dimensional area including the heart of a patient; a volume data set generation unit which generates a volume data set based on output from the ultrasonic probe; a long axis image generation unit which generates data of a long axis image of the heart from the volume data set; a display range setting unit which sets a display range against the long axis image; a short axis image generation unit which calculates a plurality of short axis sections between the start point and the end point of the display range and generates data of a plurality of short axis images concerning said plurality of calculated short axis sections; and a display unit which sequentially displays each of said plurality of short axis images.

A medical image display apparatus according to a fifth aspect of the present invention comprises: a storage unit which stores a plurality of volume data sets whose scanning times different from one another including the heart of a patient; a short axis image generation unit which respectively generates data of a plurality of short axis images concerning a predetermined short axis section of the heart based on said plurality of the volume data sets; and a display unit which displays said plurality of short axis images by changing at least one of the position and the size of each of said plurality of short axis images against a display area in accordance with variation of at least one of the position and the shape of the heart on said plurality of short axis images.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL
VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An ultrasonic diagnostic apparatus and a medical image display apparatus according to an embodiment of the present invention will now be described with reference to the drawings. Here, an organ, especially a heart, moving with time elapse in a patient is targeted for scanning by the ultrasonic diagnostic apparatus according to the present embodiment. However, the scanning target of the ultrasonic diagnostic apparatus according to the present invention is not limited to the heart, but every part of a patient is possible to be the scanning target.

Figure 1:
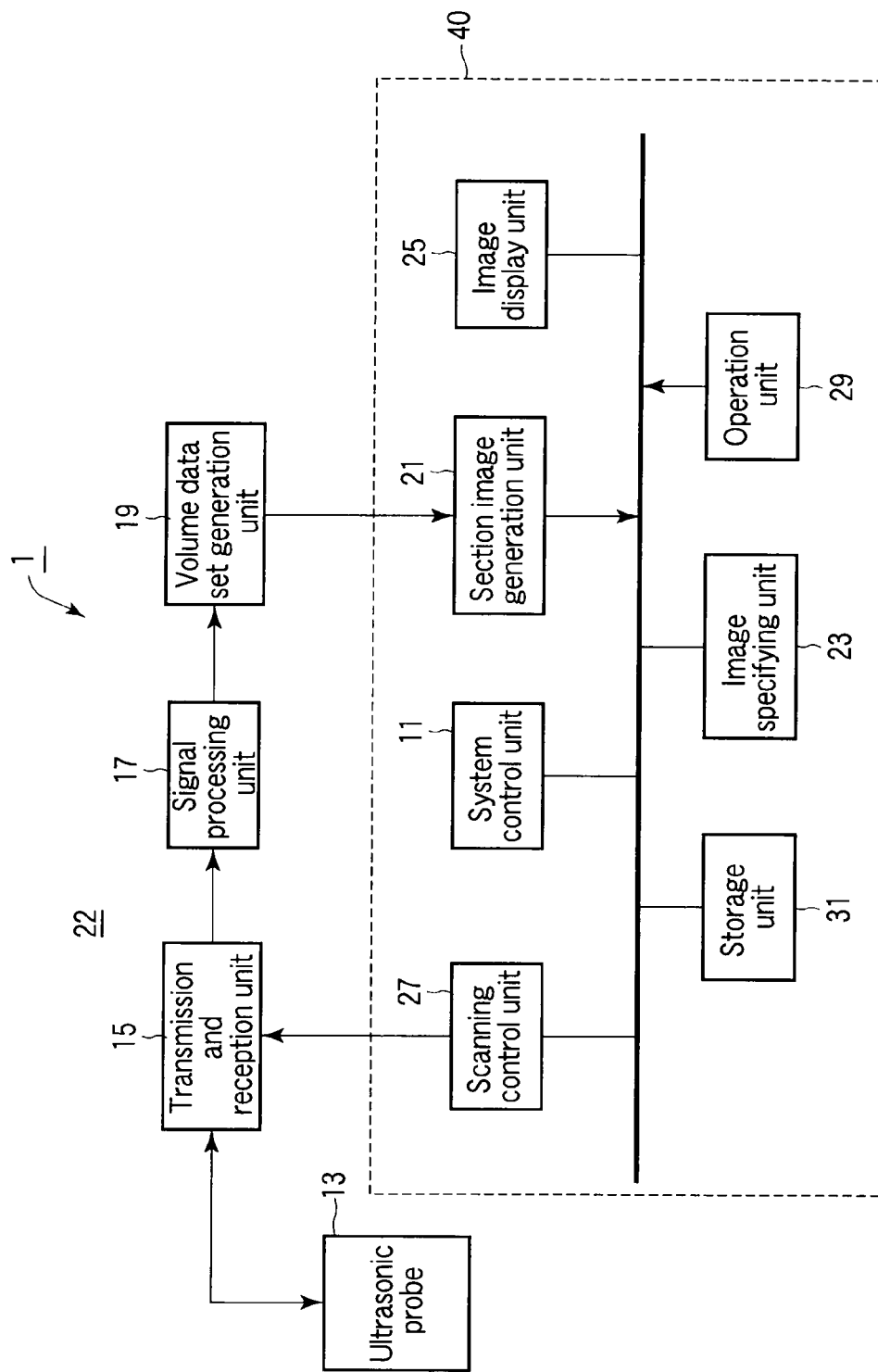
FIG. 1 is a diagram showing a arrangement of an ultrasonic diagnostic apparatus according to an embodiment of the present invention.

FIG. 1 is a diagram showing an arrangement of the ultrasonic diagnostic apparatus 1 according to the first embodiment. As shown in FIG. 1, the ultrasonic diagnostic apparatus 1 has a system control unit 11 functioning as a central unit, an ultrasonic probe 13, a transmission and reception unit 15, a signal processing unit 17, a volume data set generation unit 19, a section image generation unit 21, an image specifying unit 23, an image display unit 25, a scanning control unit 27, an operation unit 29 and a storage unit 31.

The ultrasonic probe 13 has a plurality of piezoelectric transducers which are two-dimensionally arranged. Each piezoelectric transducer generates ultrasonic waves with receiving of a drive pulse applied from the transmission and reception unit 15. The ultrasonic waves reflected by a patient and the like are received by each piezoelectric transducer as an echo signal and transmitted to the transmission and reception unit 15.

The transmission and reception unit 15 repeatedly scans a three-dimensional scanning range which includes the heart of the patient with an ultrasonic beam via the ultrasonic probe 13 under the control of the scanning control unit 27.

Specifically, the transmission and reception unit 15 has a rate pulse generation circuit, a transmission delay circuit, a drive pulse generation circuit and the like which are not illustrated by the drawings. The rate pulse generation circuit repeatedly generates a rate pulse for each channel at a predetermined rate frequency fr Hz (the cycle is 1/fr second). The delay circuit provides a delay time which is necessary for bundling the ultrasonic waves into a beam shape for each channel and determining transmission directivity to each rate pulse. The drive pulse generation circuit applies an ultrasonic drive pulse to the ultrasonic probe 13 based on the timing of the rate pulse which is delayed respectively.

Further, the transmission and reception unit 15 has an amplifier circuit, an analog-to-digital converter, a reception delay circuit, an adder and the like which are not illustrated by the drawings. The amplifier circuit amplifies the echo signal of the patient received from the ultrasonic probe 13 for each channel. The analog-to-digital converter converts the amplified echo signal from an analog signal to a digital signal for each channel. The reception delay circuit provides a delay time which is necessary for bundling into a beam shape for each channel and determining reception directivity to the echo signal converted to a digital signal. The adder performs addition of each echo signal to which the delay time is provided. With this adding process, a reflecting component from the direction corresponding to the reception directivity of the echo signal is emphasized and the ultrasonic beam is formed due to the reception directivity and the transmission directivity. One ultrasonic beam corresponds to one scanning line.

The signal processing unit 17 performs a logarithmic amplification process, an envelope detection process and the like to the echo signal which is received for each scanning line from the transmission and reception unit 15. Accordingly, B mode data in which signal strength is denoted by brightness information is generated.

The volume data set generation unit 19 three-dimensionally arranges the B mode data of each scanning line on a memory based on position information of the scanning line. A volume data set is generated by performing an interpolation process as required. The volume data set generation unit 19 performs the volume data generation process during the scanning in real time and generates a plurality of volume data sets whose scanning times different from one another.

The section image generation unit 21 generates data of a section image at an arbitrary section which is specified by an operator via the operation unit 29 and the like by performing a multi planar reformat process (MPR) to each volume data set. Specifically, as the data of the section image of the arbitrary section, the section image generation unit 21 generates data of an A section image concerning an A section, a B section image concerning a B section and a C section image concerning a C section of the volume date set.

Figure 2:
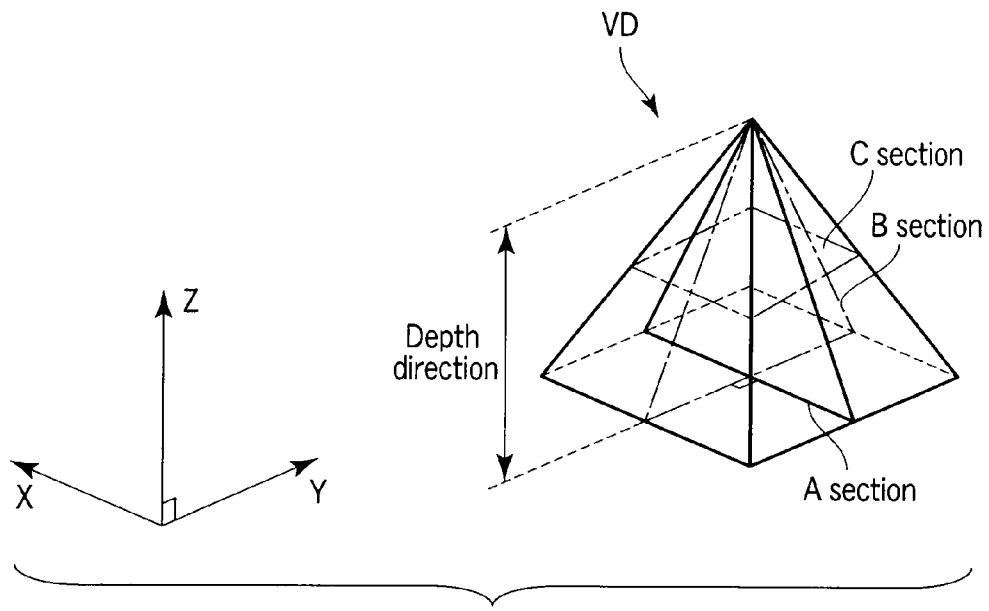
FIG. 2 is a diagram showing the positional relationship among a volume data set generated by a volume data generation unit of FIG. 1, an A section, a B section and a C section.

FIG. 2 is a diagram showing the positional relationship among the volume data set VD, the A section, the B section and the C section. As shown in FIG. 2, Z axis is defined in the depth direction of the volume data set VD and two axes which are orthogonal to Z axis are defined as X axis and Y axis. Further, a section which is parallel to an electronic scanning plane of the ultrasonic probe 13 is defined as the A section. The section which is parallel to Z axis and orthogonal to the A section is defined as the B section. The section which is orthogonal to both of the A section and the B section is defined as the C section. The A section image and the B section image are images concerning a long axis section of the heart. Further, the C section image is an image concerning a short axis section of the heart. Here, the distance from an ultrasonic transmission and reception surface of ultrasonic waves of the ultrasonic probe 13 is called a depth value.

Here, for the simplification of explanation, the section positions of the C section images which are generated from each volume data set by the section image generation unit 21 are all assumed to be at the same coordinates.

The image specifying unit 23 is connected to an electrocardiograph which is not illustrated by the drawings. The image specifying unit 23 specifies a diastole and a systole of the heart through electrocardiographic waves of the electrocardiograph. Then, the image specifying unit 23 specifies the image of the diastole and the image of the systole among the images which are generated by the section image generation unit 21.

Figure 3:
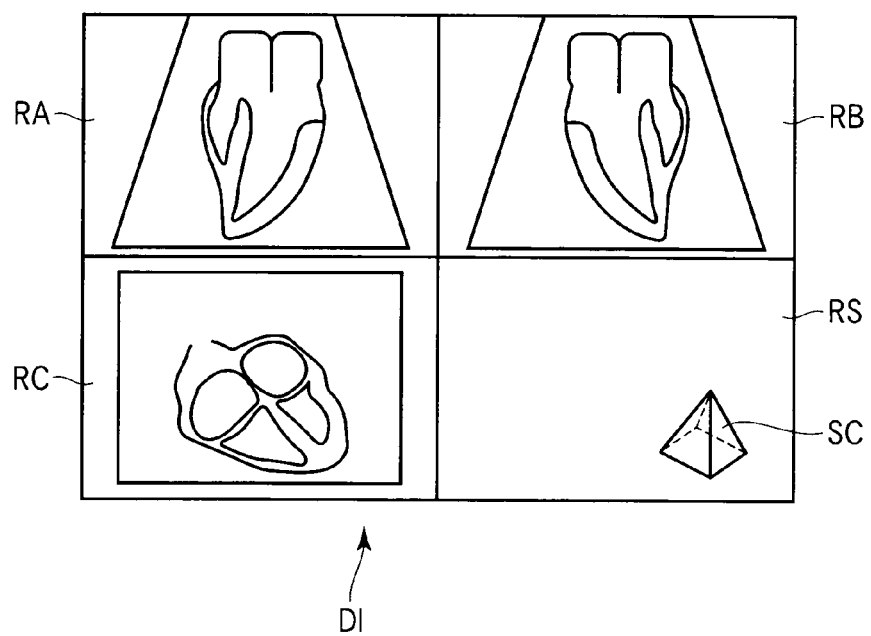
FIG. 3 is a diagram showing a display screen displayed with an image display unit of FIG. 1.

The image display unit 25 displays dynamic images of the A section image, the B section image and the C section image which are generated during the scanning in real time at each display area on a monitor. FIG. 3 is a diagram showing an example of a display screen DI. As shown in FIG. 3, the display screen DI is divided into a display area RA in which the A section image is displayed, a display area RB in which the B section image is displayed, a display area RC in which the C section image is displayed and a display area RS in which a schema SC which schematically shows the volume data set is displayed. When the C section image is displayed, the image display unit 25 performs a position adjustment process and the size adjustment process. In the position adjustment process, the image display unit 25 displays each C section image by changing the display position of the heart in the display area RC in accordance with the change of the heart position on each C section image. More specifically, the image display unit 25 displays the C section image aligning a reference point of the heart on the C section image with a reference point of the display area RC. In the size adjustment process, the image display unit 25 displays each C section image by changing the size of the heart in the display area RC in accordance with the change of the heart shape on each C section image.

The scanning control unit 27 makes the transmission and reception unit 15 scan the three-dimensional scanning range by controlling the transmission and reception unit 15 based on a control signal from the system control unit 11 or an operation signal from the operation unit 29.

The operation unit 29 accepts various commands or information inputs from an operator. A pointing device such as a mouse or a track ball, a selection device such as a mode change switch, or an input device such as a keyboard can be appropriately utilized as the operation unit 29.

The storage unit 31 stores the volume data set which is generated by the volume data set generation unit 19 and the data of various section images which are generated by the section image generation unit 21. Further, the storage unit 31 stores volume data sets and various section image data which are obtained via a network. Furthermore, the storage unit 31 stores programs and the like for performing various processes.

The system control unit 11 controls each of the structural elements so as to realize operation as the ultrasonic diagnostic apparatus 1. The system control unit 11 includes a CPU and a RAM. The system control unit 11 reads a program from the storage unit 31 and unarchives on the RAM. Then, control functions are realized with the CPU executing the process according to the program.

In the following, the operation of the ultrasonic diagnostic apparatus 1 according to the first embodiment will be described.

Figures 4A, 4B:
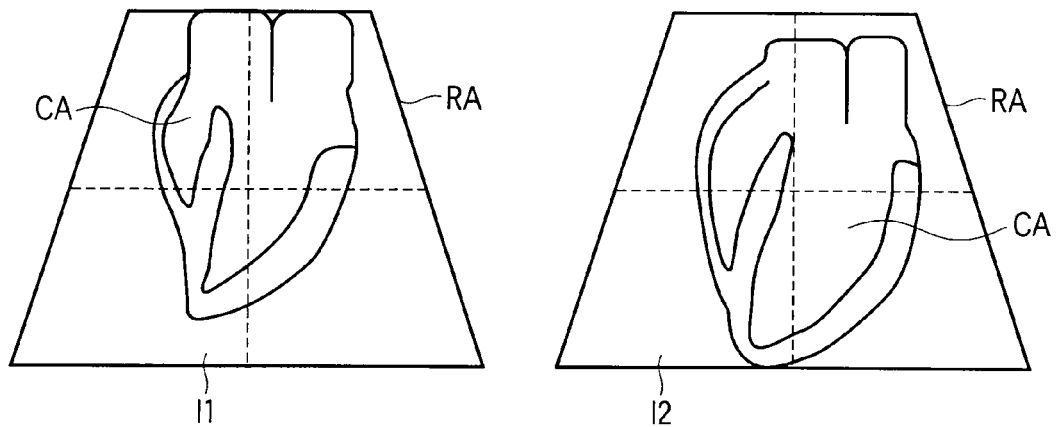
FIG. 4A is a diagram showing an example of an A section image at a systole.
FIG. 4B is a diagram showing an example of the A section image at a diastole.
Figure 5A:
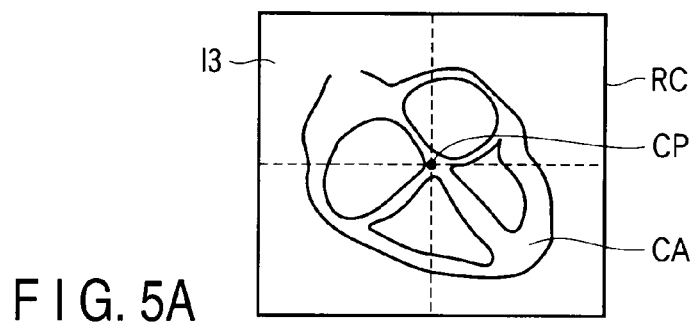
FIG. 5A is a diagram showing an example of a C section image at a systole.
Figure 5B:
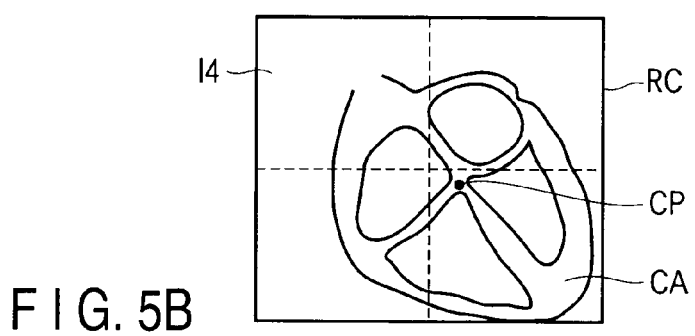
FIG. 5B is a diagram showing an example of the C section image at a diastole.

First, problems in displaying the C section image of the heart are described with reference to the drawings. During the scanning, the heart varies its spatial position and shape with time elapse by beating. FIG. 4A is a diagram showing an example of the A section image I1 at the systole. FIG. 4B is a diagram showing an example of the A section image I2 at the diastole. FIG. 5A is a diagram showing an example of the C section image I3 at the systole. FIG. 5B is a diagram showing an example of the C section image I4 at the diastole. As shown in FIGS. 4A, 4B, 5A and 5B, the heart CA varies the displayed position and shape from the systole to the diastole. Therefore, even when the center point CP of the heart CA which appears on the C section image I3 at the systole is aligned with the center of the display area RC, for example, there is a case where the center point CP of the heart CA which appears on the C section image I4 at the diastole is shifted from the center of the display area RC or a case where the heart CA protrudes from the display area RC.

Figures 6, 7:
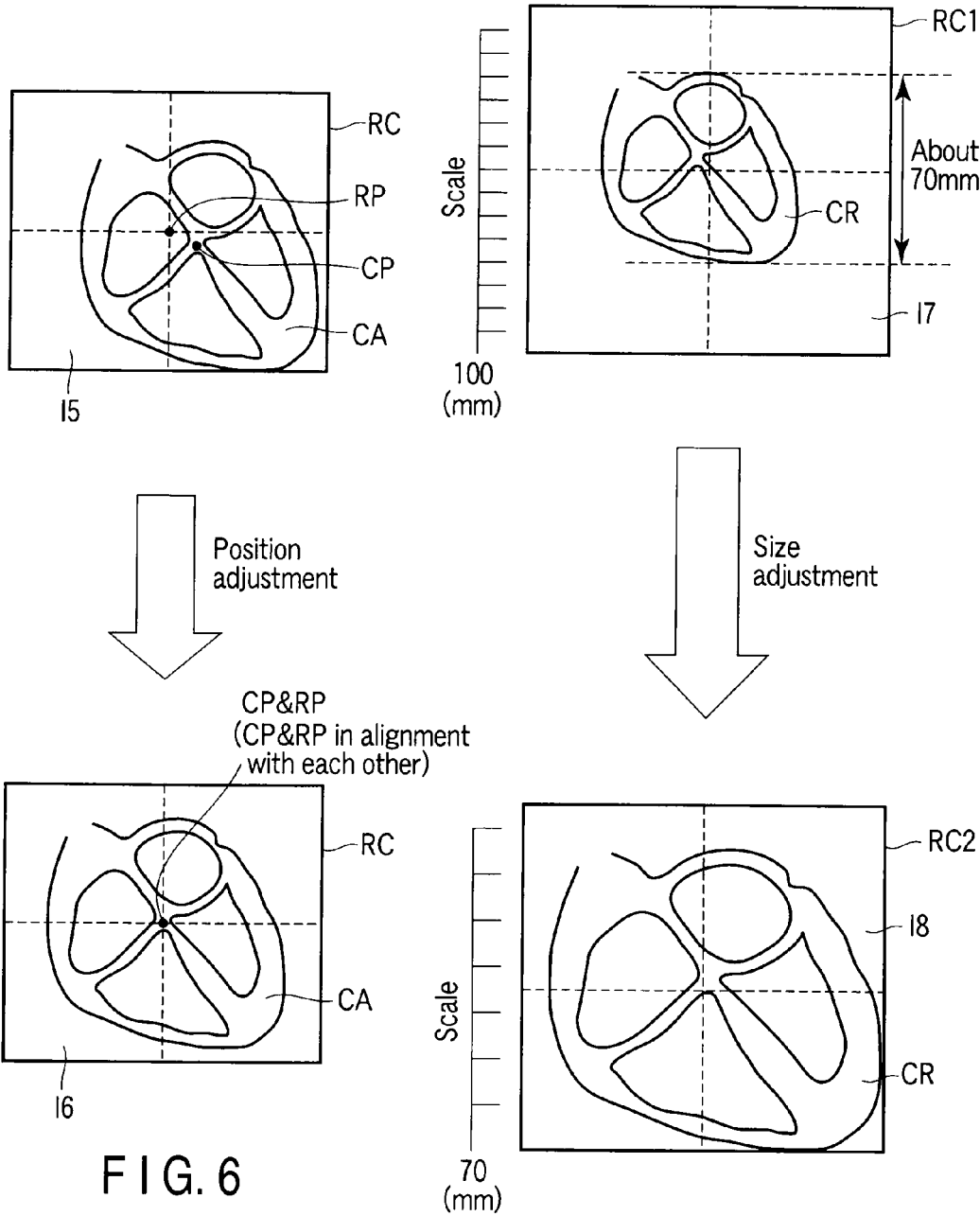
FIG. 6 is a diagram showing the C section image before performing a position adjustment process by an image display unit of FIG. 1 and the C section image after performing the position adjustment process.
FIG. 7 is a diagram showing the C section image before a size adjustment process performed by an image display unit of FIG. 1 and the C section image after the position adjustment process.

In order solve the foregoing problems, the image display unit 25 performs the position adjustment process and the size adjustment process. First, the position adjustment process by the image display unit 25 is described. FIG. 6 is a diagram showing the C section image I5 before performing the position adjustment process and the C section image I6 after performing the position adjustment process. When the data of the C section image which is to be displayed is received from the section image generation unit 21 or the image specifying unit 23, the image display unit 25 specifies the center point CP of the heart CA which appears on the C section image by utilizing conventional technology. Then, the image display unit 25 displays the C section image aligning the center point CP of the heart CA with the center RP of the display area RC.

With the position adjustment process, it becomes possible to always dynamically display the C section image aligning the center point CP of the heart with the center of the display area RC, regardless of the position variation of the heart with time elapse.

Here, the position adjustment process is described, taking the C section image as an example. However, the position adjustment process is possible to be applied to any section images, such as the A section image and B section image. Further, in the aforementioned position adjustment process, the center point of the heart and the center of the display area are aligned. However, configuration is not limited to this, and it is also possible to align an anatomically characterizing point of the heart with the center of the display area, for example. Further, the number of the characterizing point can be one or more. The number of the characterizing point can arbitrarily be set via the operation unit 29. In the case that a plurality of characterizing points are set, the image display unit 25 displays the C section image aligning the reference point which is determined based on the plurality of characterizing points specified via the operation unit 29 with the center point of the display area. The reference point is the center point of the specified plurality of characterizing points, a barycenter or the like.

In this manner, by aligning the center point CP of the heart with the center RP of the display area, it is possible to prevent shifting of the reference point of the heart from the center of the display area or protruding of the heart from the display area RC. Further, the position adjustment process is particularly effective for a diagnosis of movement observation of a specific part of the heart, such as a mitral valve, by enlarging the display. Here, it is possible to arbitrarily set via the operation unit 29 whether or not to perform the position adjustment process.

Next, the size adjustment process by the image display unit 25 will be described. As shown in FIG. 2, the shape of the volume data set is a rectangular pyramid. Therefore, the width of the X axis and the Y axis of the C section image varies in accordance with the position in the depth direction (in the Z axis direction). The maximum width of the X axis and the Y axis of the C section image is the bottom end of the volume data set. Accordingly, as shown in FIG. 7 for example, there is a case where the heart CA of about 70 mm width in full size is displayed in the display area RC1 which is set being capable of displaying up to 100 mm in full scale, depending on the position in the depth direction. In this case, since the size of the heart which appears on the display area RC1 is small compared to the size of the display area RC1, the heart is hard to be observed by an operator. Consequently, the image display unit 25 displays as matching the width of the heart CA with the width of the display area RC1 by performing the size adjustment process. For example, the image display unit 25 displays the heart of about 70 mm width in full size in the display area RC2 which is capable of displaying up to 70 mm in full scale.

In the following, specific process of the size adjustment process will be described. Here, the center point of the heart and the center of the display area are assumed to be aligned by the position adjustment process. First, when the data of the C section image at a predetermined phase of the heartbeat is received, the image display unit 25 extracts the profile of the outer wall of the heart which appears on the C section image. Typically, the predetermined phase is the phase at which the area of the heart appearing on the C section image is to be the maximum. The phase can be previously set or can be set by an operator via the operation unit 29 while observing the C section image which is displayed dynamically. Next, the image display unit 25 determines a pan value (an enlarging rate) so that the width of the extracted profile of the outer wall on the C section image and the width of the display area match. Then, the image display unit 25 displays the C section image with the determined pan value. Here, it is possible to arbitrarily switch the display based on the pan value and the normal display (synchronized display with the A section and the B section) via the operation unit 29.

With the size adjustment process, it becomes possible to dynamically display the C section image always being at an optimum size regardless of the position in the depth direction (the depth value) of the C section image.

Here, with the first embodiment, the section positions of the plurality of C section images which are dynamically displayed are all assumed to be at the same coordinates. However, the first embodiment is not limited to this. The section position of the C section image can be anatomically the same position. In this case, the image display unit 25 is capable of displaying the C section image concerning the short axis image while changing the display position and the size, etc., in accordance with the movement of the heart in the A section image and the B section image concerning the long axis section.

With the aforementioned structure, the ultrasonic diagnostic apparatus 1 becomes possible to display various section images concerning a specific part such as the heart whose position and shape vary with time elapse in accordance with variation of the position and the shape.

Second Embodiment

In the second embodiment, the ultrasonic diagnostic apparatus 1 which is featured by changing scanning line density based on a range of the heart which appears on the C section image will be described. In the following description, the structural elements having substantially identical functions to the first embodiment are assigned with identical numerals. The repeated description will be made only when necessary.

A scanning control unit 27 according to the second embodiment changes the scanning line density within a scanning range based on the range where the heart appearing on the C section image occupies and the scanning range. The scanning line density change process can be performed during the scanning in real time or can be performed after the scanning is temporally halted.

Figure 8:
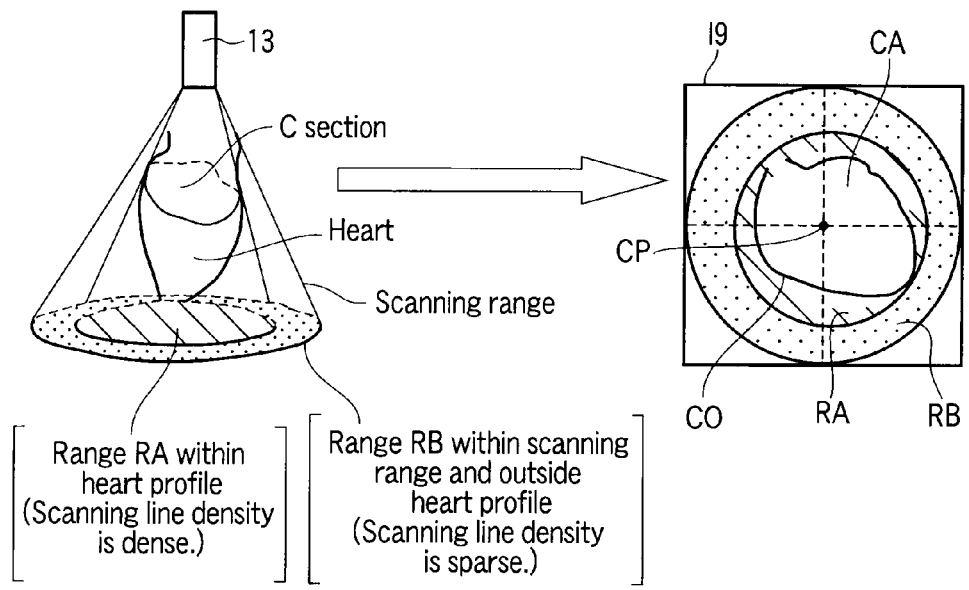
FIG. 8 is a diagram for explaining a scanning line density change process which is performed by a scanning control unit according to the second embodiment of the present invention.

FIG. 8 is a diagram for explaining the scanning line density change process. As shown in FIG. 8, the three-dimensional scanning range is scanned under the control of the scanning control unit 27. The scanning control unit 27 extracts the profile CO of the outer wall of the heart CA which appears on the C section image I9. Next, the scanning control unit 27 sets an approximately circular area RA which includes the extracted profile CO having the center point CP of the heart CA as its center. The radius of the approximately circular area RA is to be the maximum length between the center point CP and the profile CO. Then, the scanning control unit 27 sets the scanning line density of the scanning zone which corresponds to the approximately circular area RA to be dense and sets the scanning line density of a range RB which is within the scanning range and outside the approximately circular area RA to be sparse. For example, a state of setting sample points of 1024 points to each of the scanning lines of 256 lines for the reception data of one frame is assumed to be the case where the scanning line density is dense. In this case, for example, setting the sample points of each scanning line to 512 points or setting the number of scanning lines of one frame to 128 lines by thinning out the scanning lines of one frame by a line of every two lines is the case where the scanning line density is sparse. The scanning control unit 27 controls the transmission and reception unit 15 so as to perform the scanning with the scanning line density as set above. The image quality of the heart part on the C section image which is generated by the scanning with changing of the scanning line density is improved compared with the image quality of the heart part on the C section image which is generated by the scanning without changing of the scanning line density.

With the aforementioned structure, the ultrasonic diagnostic apparatus 1 changes the scanning line density based on the range of the heart which appears on the C section image. As a result, the image quality of the heart part on the C section image is improved without decreasing the frame rate.

Third Embodiment

In the third embodiment, the ultrasonic diagnostic apparatus 1 featured in that the scanning range tracks the movement of the heart on the C section image with time elapse will be described. In the following description, the structural components having substantially identical functions to the first embodiment and the second embodiment are assigned with identical numerals. The repeated description will be made only when necessary.

The scanning control unit 27 of the third embodiment changes the scanning range in accordance with the variation of the display position of the heart on the C section image with time elapse by a scanning range tracking process. The scanning range tracking process can be performed during the scanning in real time or can be performed after the scanning is temporally halted.

Figure 9:
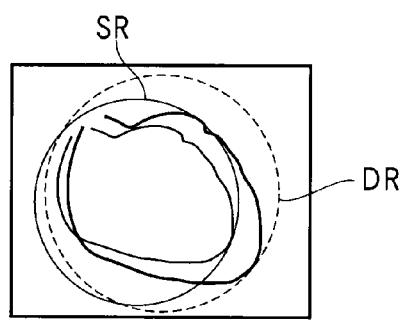
FIG. 9 is a diagram showing profiles of an outer wall of the heart on the C section image at the systole and the diastole which is generated by a section image generation unit according to the third embodiment of the present invention.

In the following, the scanning range tracking process will be described. FIG. 9 is a diagram showing profiles of the outer wall of the heart on the C section image at the systole and the diastole. As shown in FIG. 9, the display position of the heart image on the C section image varies in accordance with the beat phase. The scanning range tracking process can be performed against all the C section images which are generated in real time. However, typically, the scanning range tracking process is performed against one C section image at the systole and one C section image at the diastole. First, the scanning control unit 27 extracts the profiles of the outer wall of the heart which appears on the C section image at the systole and the diastole. Next, the scanning control unit 27 sets the approximately circular area which includes the extracted profile having the center point of the heart which appears on each of the C section images as its center. The radius of the approximately circular area is to be the maximum length between the center point and the profile. In FIG. 9, the approximately circular area SR at the systole and the approximately circular area DR at the diastole are shown as examples. Then, the scanning control unit 27 sets the range corresponding to the approximately circular area SR at the systole as the scanning range at the systole and sets the range corresponding to the approximately circular area DR at the diastole to the scanning range at the diastole.

After the setting of the scanning range, the scanning control unit 27 controls the transmission and reception unit 15 based on the set scanning range. Accordingly, the transmission and reception unit 15 becomes capable of performing the scanning while the scanning range tracks the movement of the heart with time elapse.

With the aforementioned structure, the ultrasonic diagnostic apparatus 1 makes the scanning range track the movement of the heart on the C section image with time elapse. As a result, the frame rate is improved because a needless range is not scanned.

Fourth Embodiment

In the fourth embodiment, the ultrasonic diagnostic apparatus 1 featured in that the C section image at a specified range on the A section image or the B section image is automatically replayed will be described. The automatic replay process of the C section image is the process to be performed on one volume data set. Here, the C section is assumed to be the section which intersects the A section and the B section. In the following description, the structural elements having substantially identical functions to the first embodiment and the second embodiment are assigned with identical numerals. The repeated description will be made only when necessary.

The operation unit 29 according to the fourth embodiment sets a replay start position and a replay end position of the C section image on the A section image or the B section image in accordance with a command of an operator. Typically, the replay start position and the replay end position are set by lines. The section image generation unit 21 determines the range of the C section image to be automatically replayed (hereinafter called an automatic replay range) based on the replay start position and replay end position which are set. The section image generation unit 21 calculates section positions of a plurality of the section images within the determined automatic replay range. Then, the section image generation unit 21 sequentially generates the C section images from the replay start position to the replay end position. The generated C section images are automatically replayed (displayed) with the image display unit 25. During the automatic replaying of the C section image, the image display unit 25 displays various marks which show conditions of the replaying of the C section image.

Figure 10:
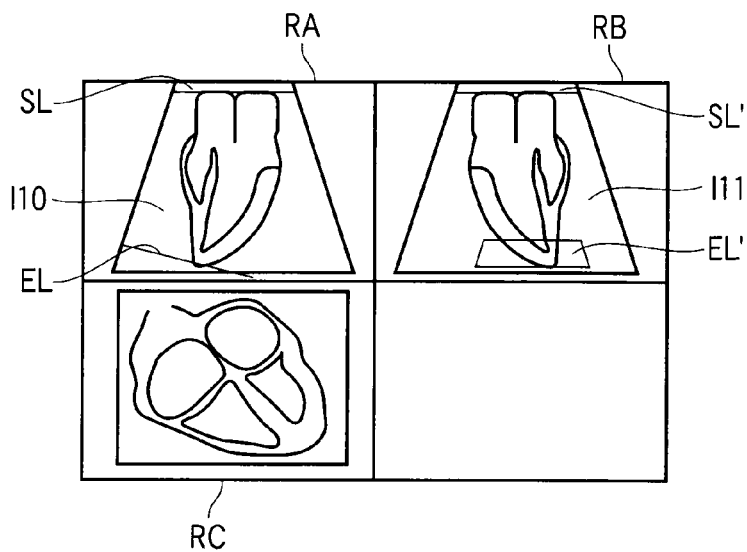
FIG. 10 is a diagram showing the replay start line and the replay end line displayed at the image display unit according to the fourth embodiment of the present invention.

Next, the automatic replay process of the C section image will be specifically described. First, the operator sets a replay start line which indicates the display starting position of the C section image and a replay end line which indicates the display end position of the C section image on the A section image or the B section image via the operation unit 29. FIG. 10 is a diagram showing the replay start line SL and the replay end line EL. As shown in FIG. 10, the operator is capable of specifying the line SL and the line EL at arbitrary positions on the A section image 110 via the operation unit 29. When the line SL and the line EL are specified on the A section image I10, the image display unit 25 displays the replay start line SL' and the replay end line EL' at the positions on the B section image Ill which respectively corresponds to the positions of the lines SL, EL. Here, the reason why the replay end line EL' is widened is that the line EL is specified being inclined on the A section image I10.

Figure 11:
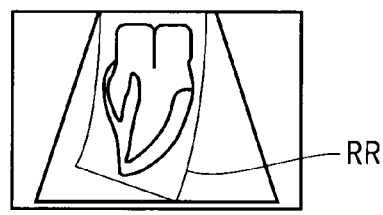
FIG. 11 is a diagram showing an automatic replay range which is determined by the section image generation unit according the fourth embodiment.

When the replay start line SL and the replay end line EL are specified, the section image generation unit 21 determines the automatic replay range based on the line SL and the line EL. The automatic replay range is determined in accordance with the shape of the heart which appears on the A section image. As shown in FIG. 11, the determined automatic replay range RR is displayed with the image display unit 25. When the automatic replay range RR is determined, the section image generation unit 21 sequentially generates the data of a plurality of the C section images (120 images, for example) within the automatic replay range RR by utilizing technology which is disclosed in Jpn. Pat. Appln. KOKAI Publication No. 2001-14495 or Jpn. Pat. Appln. KOKAI Publication No. 2001-175847, which are described above, for example. Specifically, the section image generation unit 21 extracts the long axis of the heart in the automatic replay range RR and sets a plurality of viewpoints on the extracted long axis at established intervals. Then, the section image generation unit 21 calculates the section for each viewpoint. Each calculated section's normal vector is the direction vector between the viewpoints. And then the section image generation unit 21 generates the data of the section image for each calculated section.

Figure 12:
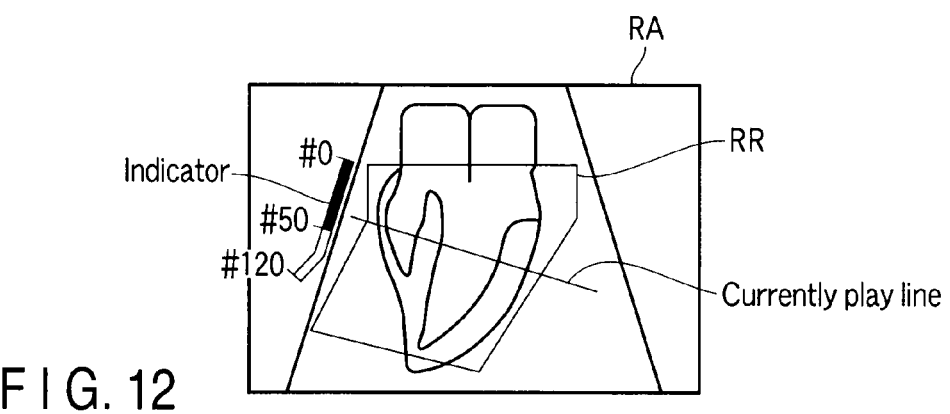
FIG. 12 is a diagram showing a mark displayed at the image display unit according to the fourth embodiment.

The plurality of generated section images are sequentially displayed at the display area of the C section image from the section image of the replay start line SL to the section image of the replay end line EL with the image display unit 25. During the automatic replaying of the C section image, the image display unit 25 displays various marks at the display area, etc., of the A section image or the B section image. FIG. 12 is a diagram showing an example of the marks. As shown in FIG. 12, a currently play line which indicates the section position of the displaying C section image is displayed superimposed on the A section image. Further, an indicator which shape is analogous to the automatic replay range RR is displayed. The indicator shows the total number of C section images which are generated by the section image generation unit 21 within the range RR, that is, the C section images which can be displayed. Further, the indicator shows a numeral indicating the displaying order of the C section image which is currently displayed. The position of the currently play line on the indicator corresponds to the section position of the C section image. Furthermore, the area on the indicator corresponding to the section position which has already been displayed and the area on the indicator corresponding to the section position which has not yet been displayed are distinctly displayed. For example, the area on the indicator corresponding to the section position which has already been displayed is displayed in black and the area on the indicator corresponding to the section position which has not yet been displayed is displayed in white.

With the structure described above, the ultrasonic diagnostic apparatus 1 automatically replays a plurality of C section images within the automatic replay range which is specified on the A section image or the B section image. As a result, efficiency of image reading is improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
    an ultrasonic probe which transmits and receives ultrasonic waves;
    a transmission and reception unit which repeatedly scans a three-dimensional scanning area including a specific part of a patient with an ultrasonic beam via the ultrasonic probe;
    a volume data set generation unit which generates a plurality of volume data sets whose scanning times differ from one another based on an output from the transmission and reception unit;
    a section image generation unit which respectively generates data of a plurality of short axis images concerning a short axis section of the specific part based on said plurality of the volume data sets; and
    a display unit which displays said plurality of section images in a display area by changing the position of each of said plurality of short axis images within the display area in accordance with the variation of the position of the specific part on said plurality of short axis images,
    wherein the transmission and reception unit extracts an outer wall profile of the specific part from each of the displayed short axis section images, sets, as a three-dimensional high-density scanning area, a three-dimensional local area included in the three-dimensional scanning area and determined from the outer wall profile, and scans the three-dimensional high-density scanning area using an ultrasonic beam emitted by the ultrasonic probe.

2. The ultrasonic diagnostic apparatus according to claim 1, wherein
    the specific part is a heart of the patient; and
    the display unit displays the short axis section images by changing a display position or a display size of each of the short axis section images on a display screen in accordance with a change with lapse of time in a position or a shape of a heart image on each of the short axis section images.

3. The ultrasonic diagnostic apparatus according to claim 1, further comprising a reference point specifying unit which specifies an anatomically characterizing reference point of a heart of the patient on the short axis image, wherein the display unit sequentially displays each of said plurality of short axis images while approximately aligning the specified reference point with a reference point in the display area.

4. The ultrasonic diagnostic apparatus according to claim 1, wherein the display unit determines an enlarging rate of the short axis image based on the size of a heart of the patient on the short axis image and displays the short axis image with the determined enlarging rate.

5. The ultrasonic diagnostic apparatus according to claim 1, further comprising a scanning control unit which controls the transmission and reception unit to scan the scanning area with a scanning line density which is determined based on the scanning area and an image region of a heart of the patient in each of the short axis section images.

6. The ultrasonic diagnostic apparatus according to claim 5,
    wherein the transmission and reception unit sets a scanning line density such that a scanning line density of the three-dimensional high-density scanning area is higher than a scanning line density of a portion of the three-dimensional scanning area other than the three-dimensional high-density scanning area, and scans the three-dimensional scanning area using an ultrasonic beam emitted by the ultrasonic probe.

7. The ultrasonic diagnostic apparatus according to claim 1, further comprising a scanning control unit which controls the transmission and reception unit to scan so that the scanning area is changed in accordance with the position of a heart of the patient on the short axis image which varies with time elapse.

8. An ultrasonic diagnostic apparatus comprising:
    an ultrasonic probe which transmits and receives an ultrasonic beam against a three-dimensional scanning area including the heart of a patient;
    a volume data set generation unit which generates a plurality of volume data sets whose scanning times different from one another based on output of the ultrasonic probe;
    a short axis image generation unit which respectively generates data of a plurality of short axis images concerning a predetermined short axis section of the heart based on said plurality of volume data sets; and
    a scanning control unit which changes scanning line density in the three-dimensional scanning area based on a range of the specific part appearing on each of said plurality of short axis images and the three-dimensional scanning area,
    wherein the scanning control unit extracts an outer wall profile of the specific part from each of the displayed short axis section images, sets, as a three-dimensional high-density scanning area, a three-dimensional local scanning area included in the three-dimensional scanning area and determined from the outer wall profile, and scans the three-dimensional high-density scanning area using an ultrasonic beam emitted by the ultrasonic probe.

9. An ultrasonic diagnostic apparatus comprising:
an ultrasonic probe which transmits and receives an ultrasonic beam against a three-dimensional scanning area including a heart of a patient;
a volume data set generation unit which generates a plurality of volume data sets whose scanning times different from one another based on output of the ultrasonic probe;
a short axis image generation unit which respectively generates data of a plurality of short axis images concerning a predetermined short axis section of the heart based on said plurality of volume data sets; and
a scanning control unit which changes the scanning area in accordance with the position variation of the heart on said plurality of short axis images with time elapse,
wherein the scanning control unit extracts an outer wall profile of the specific part from each of the displayed short axis section images, sets, as a three-dimensional high-density scanning area, a three-dimensional local area included in the three-dimensional scanning area and determined from the outer wall profile, and scans the three-dimensional high-density scanning area using an ultrasonic beam emitted by the ultrasonic probe.

10. An ultrasonic diagnostic apparatus comprising:
an ultrasonic probe which transmits and receives an ultrasonic beam against a three-dimensional area including a heart of a patient;
a volume data set generation unit which generates a volume data set based on output from the ultrasonic probe;
a long axis image generation unit which generates data of a long axis image of the heart from the volume data set;
a display range setting unit which sets a display range on the long axis image;
a short axis image generation unit which calculates a plurality of short axis sections between the start point and the end point of the display range and generates data of a plurality of short axis images concerning said plurality of calculated short axis sections;
a display unit which sequentially displays each of said plurality of short axis images; and
a scanning control unit which extracts an outer wall profile of the specific part from each of the displayed short axis section images, sets, as a three-dimensional high-density scanning area, a three-dimensional area included in the three-dimensional scanning area and determined from the outer wall profile, and scans the three-dimensional high-density scanning area using an ultrasonic beam emitted by the ultrasonic probe.

11. The ultrasonic diagnostic apparatus according to claim 10, wherein the display unit displays an indicator which indicates a position of the displayed short axis image on the long axis image.

12. The ultrasonic diagnostic apparatus according to claim 10, wherein the display unit displays at least one of the total number of said plurality of calculated short axis images and the displaying order of the displayed short axis image.

13. A medical image display apparatus connected to an ultrasonic probe, comprising:
a storage unit which stores a plurality of volume data sets whose scanning times different from one another including a heart of a patient;
a short axis image generation unit which respectively generates data of a plurality of short axis images concerning a predetermined short axis section of the heart based on said plurality of the volume data sets;
a display unit which displays said plurality of short axis images by changing the position of each of said plurality of short axis images within a display area in accordance with variation of the position of the heart on said plurality of short axis images; and
a scanning control unit which extracts an outer wall profile of the specific part from each of the displayed short axis section images, sets, as a three-dimensional high-density scanning area, a three-dimensional area included in the three-dimensional scanning area and determined from the outer wall profile, and scans the three-dimensional high-density scanning area using an ultrasonic beam emitted by the ultrasonic probe.

14. The ultrasonic diagnostic apparatus according to claim 1, wherein the specific part is a heart of a patient,
and further comprising:
a specifying unit which specifies a short axis section image in a diastolic phase of the heart and a short axis section image in a systolic phase of the heart; and
a scanning unit which extracts an outer wall profile of the specific part from the short axis section image in the diastolic phase of the heart and the short axis section image in the systolic phase of the heart, sets, as a three-dimensional high-density scanning area, a three-dimensional area included in the three-dimensional scanning area and including the outer wall profile, and causes the three-dimensional high-density scanning area to follow motion of the heart.

15. The ultrasonic diagnostic apparatus according to claim 1, further comprising a scanning unit which sets, as a three-dimensional high-density scanning area, substantially a circular area included in each of the short axis section images and including the outer wall profile and a center point of the special part.

* * * * *